(12) United States Patent
Liu et al.

(10) Patent No.: US 10,473,616 B2
(45) Date of Patent: *Nov. 12, 2019

(54) BACKSIDE CMOS COMPATIBLE BIOFET WITH NO PLASMA INDUCED DAMAGE

(71) Applicant: Taiwan Semiconductor Manufacturing Co., Ltd., Hsinchu (TW)

(72) Inventors: Yi-Shao Liu, Zhubei (TW); Chun-Ren Cheng, Hsin-Chu (TW); Ching-Ray Chen, Taipei (TW); Yi-Hsien Chang, Shetou Township (TW); Fei-Lung Lai, New Taipei (TW); Chun-Wen Cheng, Zhubei (TW)

(73) Assignee: Taiwan Semiconductor Manufacturing Co., Ltd. (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/649,963

(22) Filed: Jul. 14, 2017

(65) Prior Publication Data

US 2017/0315085 A1   Nov. 2, 2017

Related U.S. Application Data

(60) Continuation of application No. 14/799,453, filed on Jul. 14, 2015, now Pat. No. 9,709,525, which is a continuation of application No. 14/281,100, filed on May 19, 2014, now Pat. No. 9,080,969, which is a
(Continued)

(51) Int. Cl.
*G01N 27/414*   (2006.01)
*H01L 29/66*   (2006.01)
*H01L 21/311*   (2006.01)

(52) U.S. Cl.
CPC ..... *G01N 27/4145* (2013.01); *G01N 27/4148* (2013.01); *H01L 21/31105* (2013.01); *H01L 29/66477* (2013.01)

(58) Field of Classification Search
CPC combination set(s) only.
See application file for complete search history.

(56) References Cited

U.S. PATENT DOCUMENTS

| 5,702,981 | A | 12/1997 | Maniar et al. |
| 7,060,510 | B2 | 6/2006 | Bonnell et al. |
| 7,306,924 | B2 | 12/2007 | Gomez et al. |

(Continued)

FOREIGN PATENT DOCUMENTS

| CN | 100367463 | 2/2008 |
| KR | 20110037283 | 4/2011 |

(Continued)

*Primary Examiner* — Timor Karimy
(74) *Attorney, Agent, or Firm* — Sterne, Kessler, Goldstein & Fox P.L.L.C.

(57) ABSTRACT

The present disclosure provides a bio-field effect transistor (BioFET) device and methods of fabricating a BioFET and a BioFET device. The method includes forming a BioFET using one or more process steps compatible with or typical to a complementary metal-oxide-semiconductor (CMOS) process. The BioFET device includes a gate structure disposed on a first surface of a substrate and an interface layer formed on a second surface of the substrate. The substrate is thinned from the second surface to expose a channel region before forming the interface layer.

20 Claims, 13 Drawing Sheets

Related U.S. Application Data division of application No. 13/706,002, filed on Dec. 5, 2012, now Pat. No. 8,728,844.

(56) References Cited

U.S. PATENT DOCUMENTS

| | | |
|---|---|---|
| 7,632,670 B2 | 12/2009 | Offenhausser et al. |
| 7,695,609 B2 | 4/2010 | Soundarrajan et al. |
| 7,696,530 B2 * | 4/2010 | Yamamoto ......... G01N 27/4145 257/139 |
| 7,833,708 B2 | 11/2010 | Enzelberger et al. |
| 7,923,314 B2 | 4/2011 | Tezuka et al. |
| 8,007,727 B2 | 8/2011 | Shalev et al. |
| 8,420,328 B2 | 4/2013 | Chen et al. |
| 8,471,559 B2 | 6/2013 | Taherian et al. |
| 8,519,490 B2 | 8/2013 | Bikumandla |
| 8,557,643 B2 | 10/2013 | Han et al. |
| 8,728,844 B1 | 5/2014 | Liu et al. |
| 8,778,269 B2 | 7/2014 | Joshi et al. |
| 8,871,549 B2 | 10/2014 | Ellis-Monaghan et al. |
| 8,878,258 B2 | 11/2014 | Monfray et al. |
| 9,080,969 B2 | 7/2015 | Liu et al. |
| 9,389,199 B2 | 7/2016 | Cheng et al. |
| 9,417,209 B2 | 8/2016 | Shen et al. |
| 9,709,525 B2 | 7/2017 | Liu et al. |
| 2004/0185591 A1 | 9/2004 | Hsiung et al. |
| 2005/0221594 A1 | 10/2005 | Chou et al. |
| 2006/0094176 A1 | 5/2006 | Fehlhaber et al. |
| 2010/0050745 A1 | 3/2010 | Liu et al. |
| 2012/0021918 A1 * | 1/2012 | Bashir .................... B82Y 15/00 506/2 |

FOREIGN PATENT DOCUMENTS

| | | |
|---|---|---|
| KR | 101127075 | 3/2012 |
| KR | 20120129166 | 11/2012 |
| TW | 200419800 | 10/2004 |
| TW | 200532192 | 10/2005 |
| TW | 200532907 | 10/2005 |
| WO | WO 2008/068719 | 6/2008 |

* cited by examiner

BACKSIDE CMOS COMPATIBLE BIOFET WITH NO PLASMA INDUCED DAMAGE

PRIORITY CLAIM

This application is a continuation of U.S. patent application Ser. No. 14/799,453, filed on Jul. 14, 2015, now U.S. Pat. No. 9,709,525 issued on Jul. 18, 2017 and entitled "Backside CMOS Compatible BioFET with No Plasma Induced Damage" which is a continuation of U.S. patent application Ser. No. 14/281,100, filed on May 19, 2014, now U.S. Pat. No. 9,080,969 issued on Jul. 14, 2015 and entitled "Backside CMOS Compatible BioFET with No Plasma induced Damage" which is a divisional of U.S. patent application Ser. No. 13/706,002, filed Dec. 5, 2012, now U.S. Pat. No. 8,728,844 issued on May 20, 2014 and entitled "Backside CMOS Compatible BioFET with No Plasma Induced Damage," which applications are incorporated herein by reference.

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs) and MEMS.

BioFETs (biologically sensitive field-effect transistors, or bio-organic field-effect transistors) are a type of biosensor that includes a transistor for electrically sensing biomolecules or bio-entities. While BioFETs are advantageous in many respects, challenges in their fabrication and/or operation arise, for example, due to compatibility issues between the semiconductor fabrication processes, the biological applications, restrictions and/or limits on the semiconductor fabrication processes, integration of the electrical signals and biological applications, and/or other challenges arising from implementing a large scale integration (LSI) process.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1A:
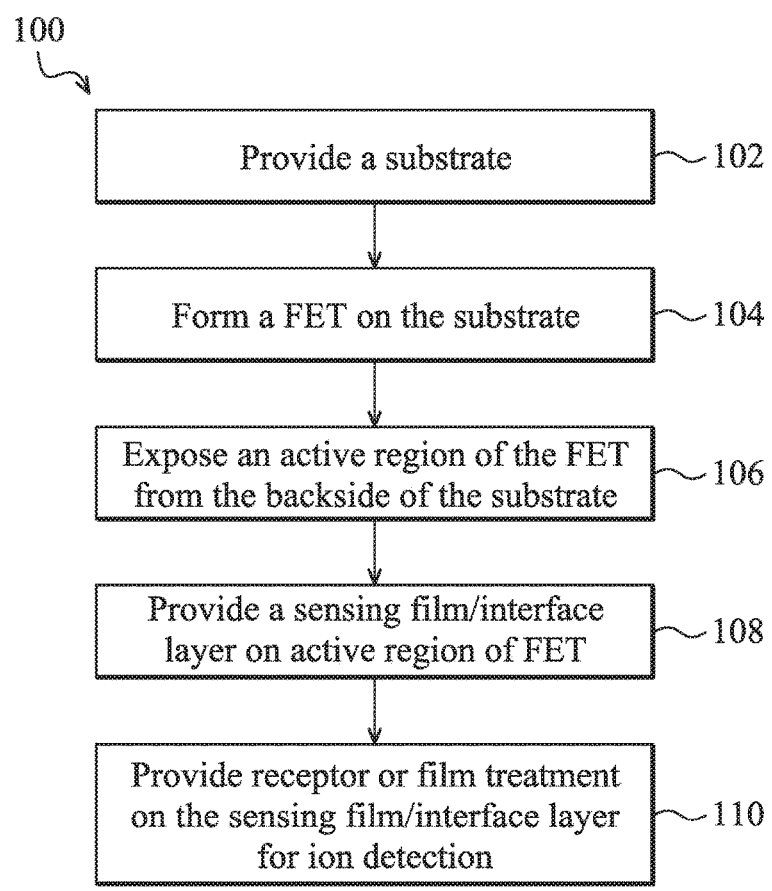
FIGS. 1A-1C are flow charts of various embodiments of methods of fabricating a BioFET device according to one or more aspects of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Further still, references to relative terms such as "top", "front", "bottom", and "back" are used to provide a relative relationship between elements and are not intended to imply any absolute direction. Various features may be arbitrarily drawn in different scales for simplicity and clarity.

In a biological field-effect transistor (BioFET), the gate of a metal-oxide-semiconductor field-effect transistor (MOSFET), which controls the conductance of the semiconductor between its source and drain contacts, is replaced by a bio- or biochemical-compatible layer or a biofunctionalized layer of immobilized probe molecules that act as surface receptors. Essentially, a BioFET is a field-effect biosensor with a semiconductor transducer. A decided advantage of BioFETs is the prospect of label-free operation. Specifically, BioFETs enable the avoidance of costly and time-consuming labeling operations such as the labeling of an analyte with, for instance, fluorescent or radioactive probes.

A typical detection mechanism for BioFETs is the conductance modulation of the transducer due to the binding of a target biomolecule or bio-entity to a sensing surface or a receptor molecule immobilized on the sensing surface of the BioFET. When the target biomolecule or bio-entity is bonded to the sensing surface or the immobilized receptor, the drain current of the BioFET is varied by the potential from the sensing surface. This change in the drain current can be measured and the bonding of the receptor and the target biomolecule or bio-entity can be identified. A great variety of biomolecules and bio-entities may be used to functionalize the sensing surface of the BioFET such as ions, enzymes, antibodies, ligands, receptors, peptides, oligonucleotides, cells of organs, organisms and pieces of tissue. For instance, to detect ssDNA (single-stranded deoxyribonucleic acid), the sensing surface of the BioFET may be functionalized with immobilized complementary ssDNA strands. Also, to detect various proteins such as tumor markers, the sensing surface of the BioFET may be functionalized with monoclonal antibodies.

One example of a biosensor has a sensing surface is a top of a floating gate connected to the gate of the BioFET. The floating gate is connected to the gate structure of the BioFET though a stack of metal interconnect lines and vias (or multi-layer interconnect, MLI). The various metal layers over the gate electrode can also contribute to damage by antenna effect during the MLI formation process. In such a BioFET, the potential-modulating reaction takes place at an outer surface of the final (top) metal layer or a dielectric surface formed on top of the MLI and is sensed indirectly by the BioFET. This embodiment may be disadvantageous however, in that the sensitivity of the device is decreased due to the presence of parasitic capacitances associated with the MLI. As result a minimum sensing plate dimension is usually specified so that a sufficiently detectable amount of potential-modulating reaction can take place. The minimum sensing plate dimension in turn limits the BioFET density.

In another example, the biomolecules bind directly or through receptors on the gate or the gate dielectric of the BioFET. These "direct sensing" BioFETs directly senses the target biomolecules without the parasitic capacitances associated with MLI. Its construction requires removal of the MLI material above the BioFET to form a sensing well and exposes the gate electrode or gate dielectric to the fluidic environment where potential-modulating surface reactions occur. These BioFETs are more sensitive than the floating gate types but are challenging to construct for several reasons. The sensing well etched has a high aspect ratio, for example, 30 or greater, so it is usually performed with high energy plasma etch. The high-aspect ratio of the sensing well also limits the profile of the etched sensing well. The high energy plasma etch can damage the gate electrode due to charge-induced damage. One attempt in reducing the aspect ratio of the sensing well to make the etch easier results in limitation of the number of metal layers, down to one or two metal layers. The reduction in metal layers limits the interconnect routing and integration options of the device, for example, the number and type of circuits for controlling the BioFET. The process is also very sensitive to alignment, because misalignment may expose the metals in the MLI surrounding sensing well or cause the sensing surface area to be less than designed.

In yet another example, the biomolecules are placed close to the gate from a backside of the substrate. In this example, a sensing surface is formed on the backside of the transistor gate through backside of the substrate. This example avoids the difficulty of having to etch through multiple layers of interconnects and yet placing the biomolecules close enough to the gate to have much higher sensitivity than the floating gate biosensor. Illustrated in FIG. 1 is a method 100 of fabricating a bio-organic field effect transistor (BioFET). The method 100 may include forming a BioFET using one or more process steps compatible with or typical to a complementary metal-oxide-semiconductor (CMOS) process. It is understood that additional steps can be provided before, during, and after the method 100, and some of the steps described below can be replaced or eliminated, for additional embodiments of the method. Further, it is understood that the method 100 includes steps having features of a typical CMOS technology process flow and thus, are only described briefly herein.

Figure 2:
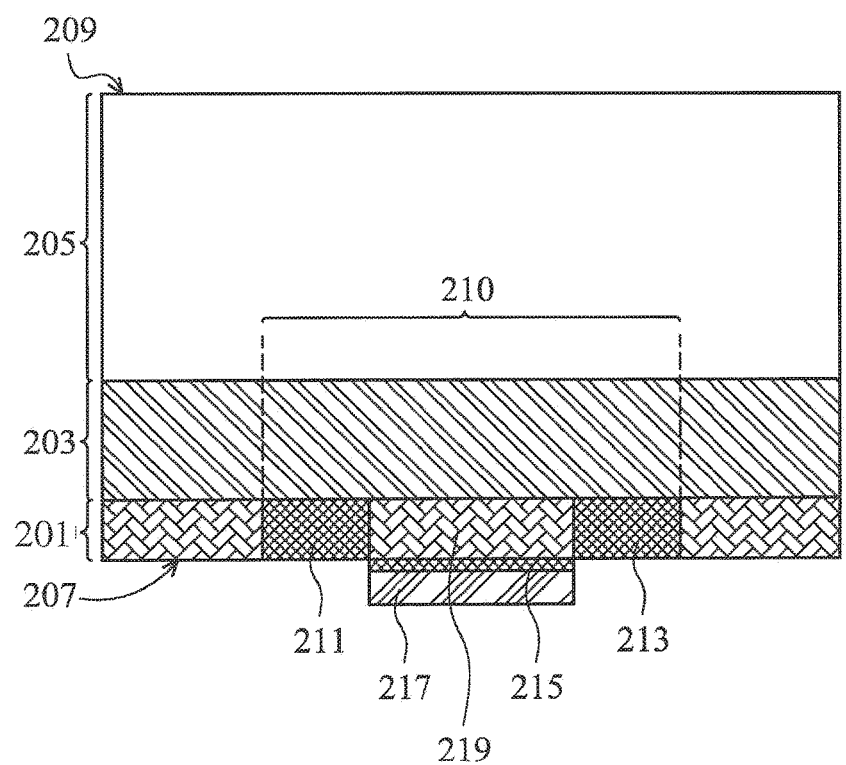
FIGS. 2-4, 5A, 5B, 6A, 6B, 7A, 7B, 8A, 8B, 8C, 8D, 9A, 9B, and 9C are cross-sectional views of partially fabricated BioFET devices constructed according to one or more steps of the method of FIGS. 1A to 1C.

The method 100 begins at block 102 where a substrate is provided. The substrate may be a semiconductor substrate. The semiconductor substrate may be a silicon substrate. Alternatively, the substrate may comprise another elementary semiconductor, such as germanium; a compound semiconductor including silicon carbide; an alloy semiconductor including silicon germanium; or combinations thereof. In some embodiments, the substrate is a semiconductor on insulator (SOI) substrate. As shown in FIG. 2, the SOI substrate may include a buried oxide (BOX) layer 203 formed by a process such as separation by implanted oxygen (SIMOX), and/or other suitable processes. The SOI substrate also includes a first semiconductor layer 201 and a second semiconductor layer 205 on either side of the BOX layer 203. A first surface or a first side 207 of the SOI substrate is the device side where the gate of the FET is formed. A second surface or a second side 209 of the SOI is the backside from which the substrate will be thinned in a subsequent operation. The substrate may include doped regions, such as p-wells and n-wells. In the present disclosure, a wafer is a workpiece that includes a semiconductor substrate and various features formed in and over and attached to the semiconductor substrate. The wafer may be in various stages of fabrication and is processed using the CMOS process. After the various stages of fabrication are completed, the wafer is separated into individual dies that are packaged into an integrated chip.

Referring back to FIG. 1A, the method 100 then proceeds to block 104 where a field effect transistor (FET) 210 is formed on the first side 207 of the substrate. The FET 210 may include a gate structure (including dielectric 215 and electrode 217), a source region (211 or 213), a drain region (211 or 213), and a channel region 219 interposing the source and drain regions (211 and 213). The source, drain, and/or channel region are formed on an active region of the semiconductor substrate. The active region is a part of the semiconductor layer 201. The FET 210 may be an n-type FET (nFET) or a p-type FET (pFET). For example, the source/drain regions may comprise n-type dopants or p-type dopants depending on the FET configuration. The gate structure may include a gate dielectric layer 215, a gate electrode layer 217, and/or other suitable layers. In an embodiment, the gate electrode 217 is polysilicon. Other exemplary gate electrodes include metal gate electrodes including metal such as, Cu, W, Ti, Ta, Cr, Pt, Ag, Au; suitable metallic compounds like TiN, TaN, NiSi, CoSi; combinations thereof; and/or other suitable conductive materials. In an embodiment, the gate dielectric is silicon oxide. Other exemplary gate dielectrics include silicon nitride, silicon oxynitride, a dielectric with a high dielectric constant (high k), and/or combinations thereof. Examples of high k materials include hafnium silicate, hafnium oxide, zirconium oxide, aluminum oxide, tantalum pentoxide, hafnium dioxide-alumina ($HfO_2$—$Al_2O_3$) alloy, or combinations thereof. The FET may be formed using typical CMOS processes such as, photolithography; ion implantation; diffusion; deposition including physical vapor deposition (PVD), metal evaporation or sputtering, chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), atomic layer CVD (ALCVD), spin on coating; etching including wet etching, dry etching, and plasma etching; and/or other suitable CMOS processes.

Figure 3:
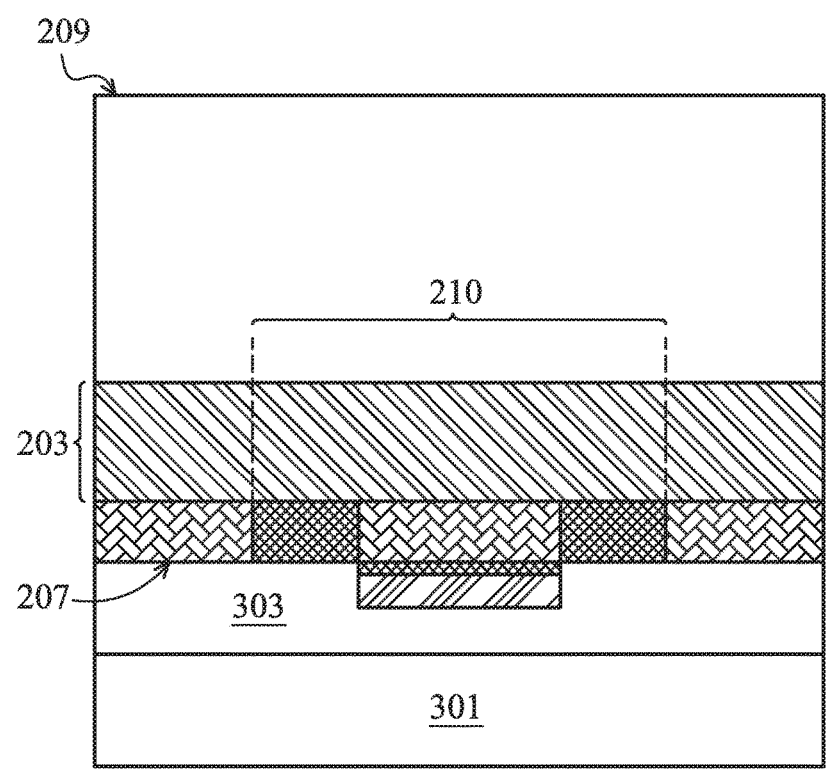

The method 100 may include forming additional layers over the PET including metal interconnect layers, dielectric layers, passivation layers, bonding metal layers, and any other material layers typically formed in complete a semiconductor device. In FIG. 3, a layer 303 is disposed over the FET between the FET and a carrier substrate 301. The layer 303 may include a multi-layer interconnect (MLI) structure. The MLI structure may include conductive lines, conductive vias, and/or interposing dielectric layers (e.g., interlayer dielectric (ILD)). The MLI structure may provide physical and electrical connection to the FET 210 at the source and drain 211 and 213 and at the gate electrode 217. The conductive lines may comprise copper, aluminum, tungsten, tantalum, titanium, nickel, cobalt, metal silicide, metal nitride, poly silicon, combinations thereof, and/or other materials possibly including one or more layers or linings. The interposing or inter-layer dielectric layers (e.g., ILD layer(s)) may comprise silicon dioxide, fluorinated silicon glass (FGS), SILK (a product of Dow Chemical of Michigan), BLACK DIAMOND (a product of Applied Materials of Santa Clara, Calif.), and/or other insulating materials. The MLI may be formed by suitable processes typical in CMOS fabrication such as CVD, PVD, ALD, plating, spin-on coating, and/or other processes.

If used, a carrier substrate 301 allows various subsequent operations on the backside 209 of the semiconductor substrate without affecting the structural integrity of the semiconductor substrate. The carrier substrate 301 is attached to the semiconductor substrate by bonding. In some embodiments, the carrier substrate is bonded to the last MLI layer. In an embodiment, the carrier substrate is bonded to a passivation layer formed on the MLI and/or ILD layers of the substrate. The carrier substrate may be attached to the device substrate using fusion, diffusion, eutectic, and/or other suitable bonding methods. Exemplary compositions for the carrier substrate include silicon, glass, and quartz. In some embodiments, the carrier substrate 301 may include other functionality such as; interconnect features, bonding sites, defined cavities, and/or other suitable features. The carrier substrate may be removed during subsequent processing (e.g., after thinning).

The method 100 then proceeds to block 106 where an active region of the FET is exposed from the backside of the substrate. Depending on the type of substrate a number of methods may be used to expose the active region, which usually includes a channel region of the FET. According to various embodiments, the substrate is thinned from a backside. A first thinning may be accomplished by grinding, wet etch, dry etch, plasma etch and/or other suitable processes. In order to avoid plasma induced damage (PID) with residual charge at the active region of the FET, a non-plasma etch is used in this operation or at least as the last thinning step. Thus in some embodiments, a wet etch or a non-plasma dry etch is used to thin the entire substrate from the backside to the active region. In other embodiments, a first thinning, which may include plasma etch, is performed first to reduce the thickness of the substrate and a last etch operation uses a non-plasma etch to expose the active region at the backside of the substrate.

Figure 1B:
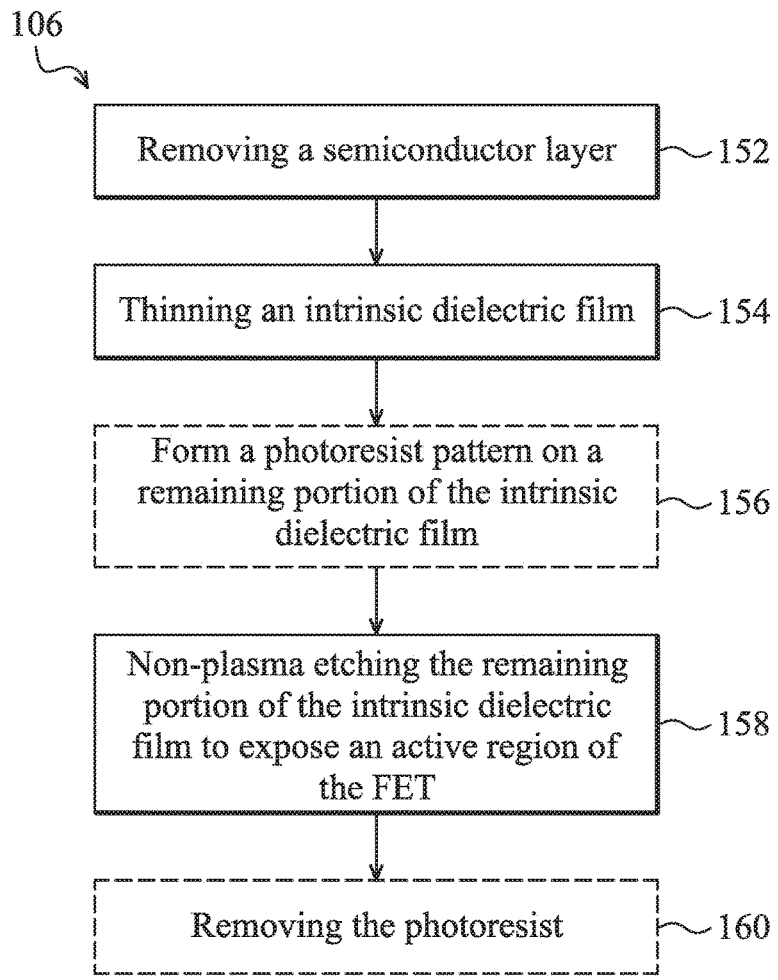
Figure 4:
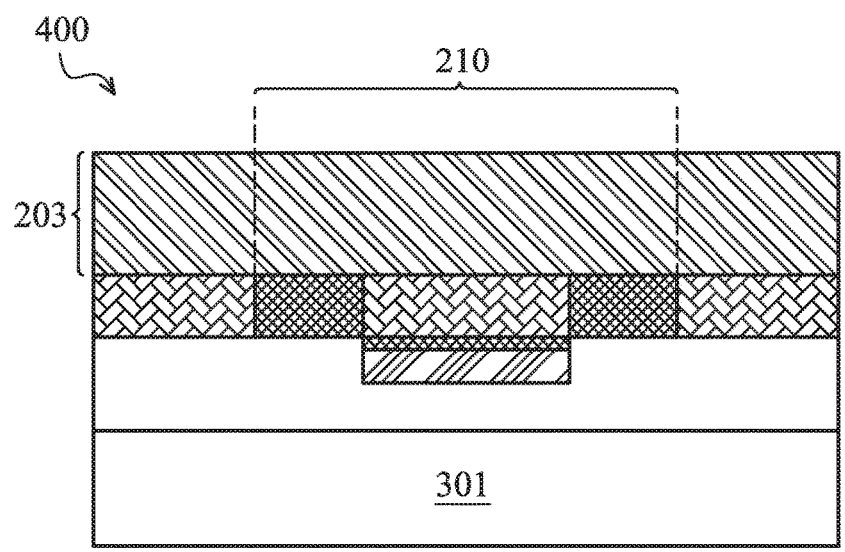

FIG. 1B is a flow chart showing block 105 of method 100 in accordance with various embodiments of the present disclosure pertaining to when the substrate is a silicon-on-insulator (SOI) substrate. A SOI substrate has an intrinsic dielectric film, sometimes referred to as the buried oxide (BOX) layer, between two semiconductor layers. The FET is formed in a first semiconductor layer, which is usually thinner than a second semiconductor layer on an opposite side of the intrinsic dielectric film. The second semiconductor layer is removed. In block 152 of FIG. 1B, a semiconductor layer is removed from the SOI substrate. The removed semiconductor layer is the semiconductor layer opposite from the FETs formed in block 104. The removal may be accomplished by mechanical or chemical means. For example, mechanical means includes polishing or grinding, such as chemical mechanical polishing (CMP). A chemical means includes wet etch, such as HNA or TMAH or dry etch including plasma and non-plasma etch. FIG. 4 shows a wafer 400 after a semiconductor layer 205 from FIG. 3 is removed. The wafer 400 includes the intrinsic dielectric layer 203 and the carrier substrate 301 on either side of the FET 210.

Figure 5A:
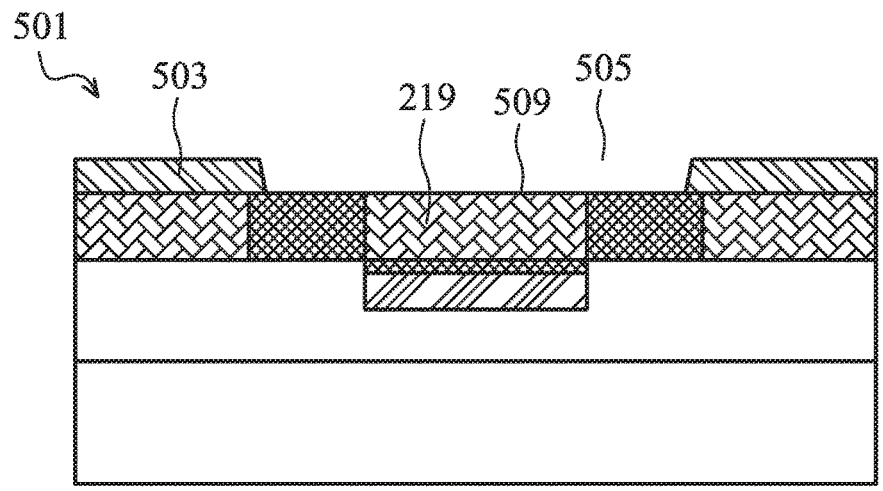

In block 154 of FIG. 1B, the intrinsic dielectric film is thinned. The intrinsic dielectric film may be a silicon oxide layer between about a few nanometers to several hundred nanometers. In some embodiments, the intrinsic dielectric layer is thinned by using wet etch, such as buffered oxide etch (BOE), or a non-plasma dry etch. The intrinsic dielectric layer may be partially removed, such as the intrinsic dielectric layer 503 shown in FIG. 5A, or completely removed, such as the embodiment shown in FIG. 5B. If the intrinsic dielectric layer is partially removed, then a plasma-etch may be used for the thinning. In some embodiments, the intrinsic dielectric layer is thinned to about 2000 angstroms or less.

According to various embodiments, after a partial thinning of the intrinsic dielectric layer in block 154, a photoresist pattern is formed on a remaining portion of the intrinsic dielectric layer in block 154. The photoresist pattern protects some of the intrinsic dielectric layer from a subsequent non-plasma etch to expose an active region of the FET in block 158. The non-plasma etch may be a wet etch or a dry etch that does not involve plasma. The non-plasma etch forms a trench 505 having a bottom exposing the channel region 219 of the FET 210. A non-plasma etch is used to avoid plasma-induced damage at the exposed surface 509 of the channel region 219. By thinning the intrinsic dielectric layer 203 first, the trench 505 has a low aspect-ratio, for example, less than about 5 or even about 1 or less. The low aspect-ratio allows fine profile control during the etch and avoid forming sharp corners that can impede sensing film uniformity. In some embodiments, the sidewall profile of the trench 505 is substantially straight.

Figure 5B:
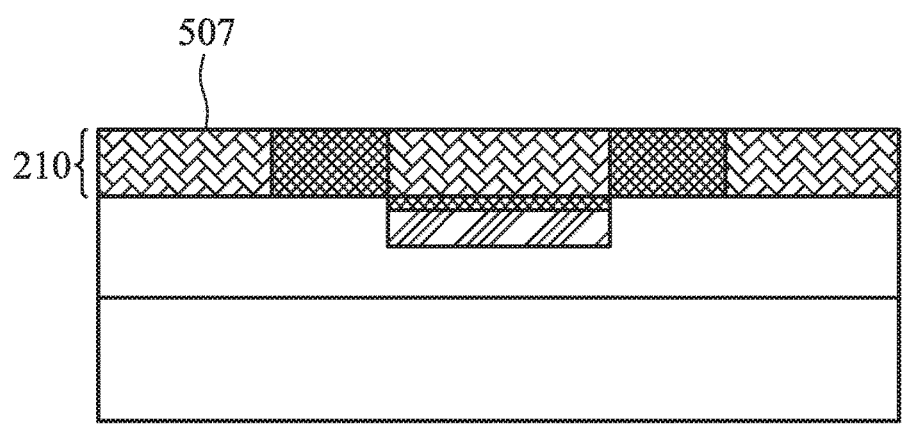

According to some embodiments as shown in FIG. 5B, the intrinsic dielectric layer 203 is completely removed and the first semiconductor layer 201 is exposed at surface 507. The complete removal may occur in one or more operations such as blocks 154 and 158 of FIG. 1B. However, the last operation which exposes the surface 507 cannot involve plasma etch so as to avoid plasma-induced damage (PID) to surface 507.

If a photoresist pattern was formed in block 156, then in block 150 the photoresist is removed. A PID-less photoresist removal process such as stripping and ozone ashing may be used. Because the exposed surface 509 of the trench 505 and the exposed surface 507 of the first semiconductor layer 201 are susceptible to plasma-induced damage (PID), some plasma ashing processes may not be used to remove the photoresist pattern.

Figure 1C:
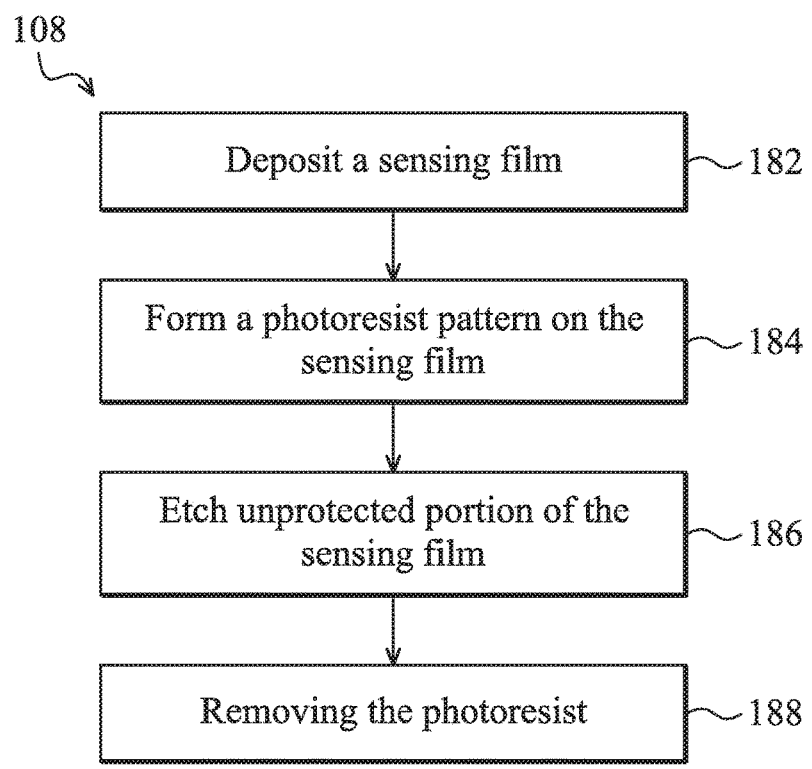

Referring back to FIG. 1A, in block 108 an interface layer is formed in the opening. FIG. 1C is flow chart showing block 108 of method 100 in accordance with various embodiments of the present disclosure. In block 182 of FIG. 1C, a sensing film is deposited over the wafer. The sensing film may be formed on the exposed surface 509 of the trench 505 and the exposed surface 507 of the first semiconductor layer 201. Also referred to herein as the interface layer, the sensing film is compatible (e.g., friendly) for biomolecules or bio-entities binding. For example, the sensing film may provide a binding interface for biomolecules or bio-entities. The sensing film may include a dielectric material, a conductive material, and/or other suitable material for holding a receptor. Exemplary interface materials include high-k dielectric films, metals, metal oxides, dielectrics, and/or other suitable materials. As a further example, exemplary sensing film materials include $HfO_2$, $Ta_2O_5$, Pt, Au, W, Ti, Al, Cu, oxides of such metals, $SiO_2$, $Si_3N_4$, $Al_2O_3$, $TiO_2$, TIN, $ZrO_2$, SnO, $SnO_2$; and/or other suitable materials. The sensing film may be formed using CMOS processes such as, for example, physical vapor deposition (PVD) (sputtering), chemical vapor deposition (CVD), plasma-enhanced chemical vapor deposition (PECVD), atmospheric pressure chemical vapor deposition (APCVD), low-pressure CVD (LP-CVD), high density plasma CVD (HDPCVD), or atomic layer CVD (ALCVD). In embodiments, the sensing film includes a plurality of layers.

Figure 6A:
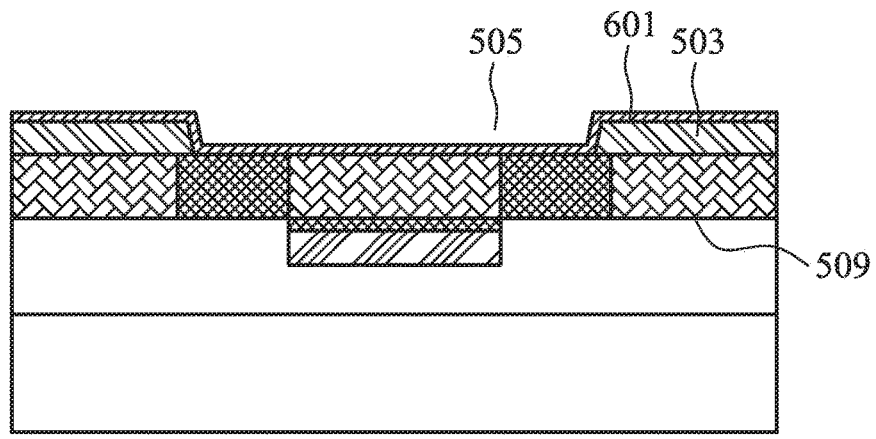
Figure 6B:
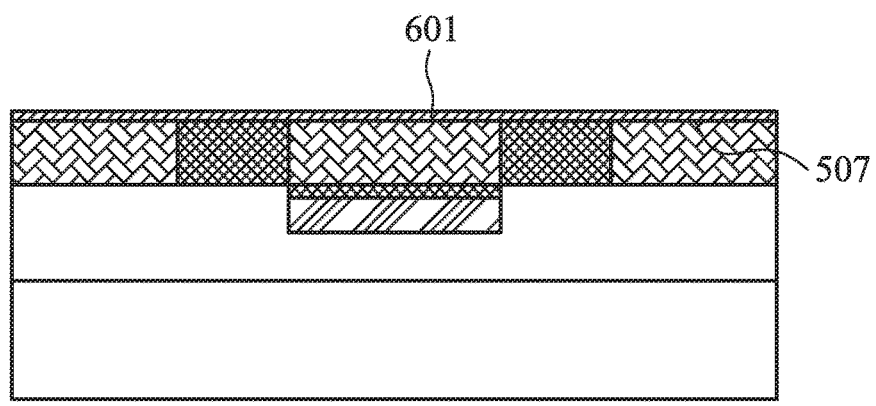

FIGS. 6A and 6B shows a sensing film formed on the exposed surface 509 of the trench 505 (FIG. 6A) and the exposed surface 507 of the first semiconductor layer 201 (FIG. 6B). In FIG. 6A, the sensing film is deposited over the wafer on the field area above the remaining intrinsic dielectric layer 503 and sidewalls and bottom of trench 505. In FIG. 6B, the sensing film is deposited over the wafer over the entire surface 507 of the semiconductor layer.

Figure 7A:
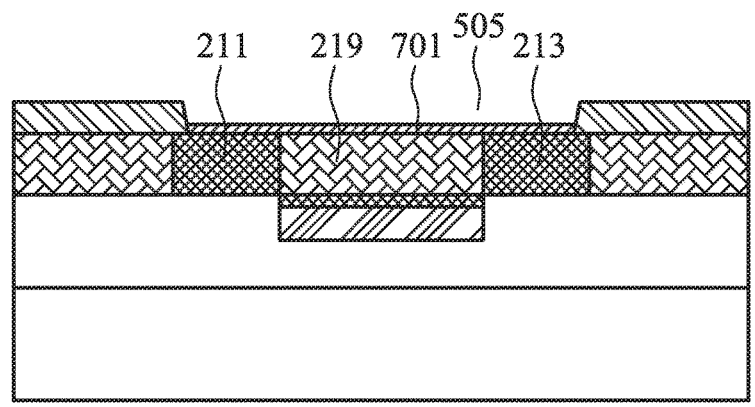
Figure 7B:
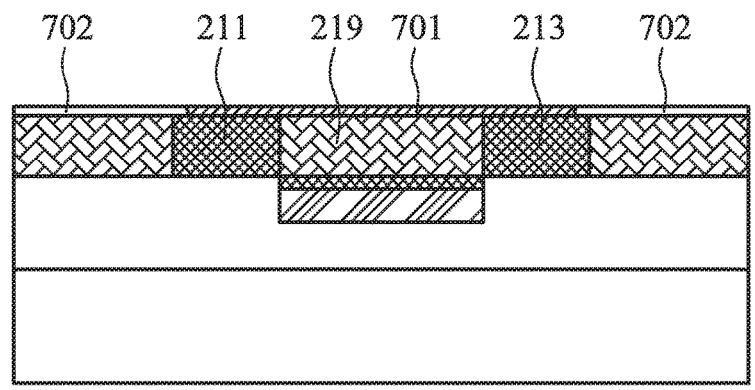

Referring back to FIG. 1C, in block 184, a photoresist pattern is formed over the sensing film to protect a portion of the sensing film. The portion over the channel region of the FET is protected. Unprotected portions of the sensing film is removed in an etch process in block 186. The etch process may involve any known etch process including plasma etch, since the portion susceptible to PID is protected, FIGS. 7A and 7B shows a sensing film 701 remaining on the respective surfaces. In FIG. 7A, sensing film 701 is shown only at the bottom surface of trench 505; however, in some embodiments the sidewalls of the trench 505 may also be covered with sensing film 701. The sensing film 701 completely covers the channel region 219 and partially covers the source and drain region 211 and 213. The partial coverage of the source and drain region may be adjusted based on the FET design and area requirements for the sensing film 701. In FIG. 7B, the sensing film 701 completely covers the channel region 219 and partially covers the source and drain region 211 and 213. In order to prevent unspecified binding of biomolecules on surfaces others than a sensing film, a blocking layer or a passivating layer 702 may be deposited. A passivating layer 702 may be silicon nitride, silicon oxide, or other solid-state dielectric layers. A blocking agent, which may be solid or liquid on which a bio-molecule cannot bind or has low affinity, may be used in forming passivating layer 702. One example is hexamethyldisiloxane (HMDS). In another example, a protein such as a Bovine Serum Albumin (BSA) is used as the blocking agent. The blocking layer/passivating layer 702 may be thicker or thinner than the sensing film 701.

After etching and optionally adding a passivating or blocking agent, the photoresist is removed in block 188 in a PID-free photoresist removal process. In some embodiments, the sensing film 601 is not patterned and etched and remains over the respective surfaces of the FET.

Referring back to FIG. 1A, in block 110 a film treatment or a receptor such as an enzyme, antibody, ligand, peptide, nucleotide, cell of an organ, organism, or piece of tissue is provided or bound on an interface layer/sensing film for detection of a target biomolecule. For instance, to detect ssDNA (single-stranded deoxyribonucleic acid), the sensing film may be functionalized with immobilized complementary ssDNA strands. Also, to detect various proteins such as tumor markers, the sensing film may be functionalized with monoclonal antibodies. The receptors may be a part of self-assembled monolayer (SAM) of molecules. The SAM may have head groups of silane groups, silyl groups, silanol groups, phosphonate groups, amine groups, thiol groups, alkyl groups, alkene groups, alkyne groups, azide groups, or expoxy groups. The receptors are attached to the head groups of SAM.

In some embodiments, the sensing film is treated or modified with a coating or chemistry to affect its chemical functionality. For example, the sensing film may be treated to have a hydrophilic or hydrophobic surface. In other examples, the sensing film may be modified to have certain conductance or magnetic properties. The film treatment or receptor may be produced by adsorption from solution either from a wet tank or stamping and certain types of depositions such as sputtering or gaseous deposition. The receptors may be patterned, for example, by using a micro-contact printing, dip-pen nanolithography, or by selectively removing receptors after attaching. When attached to the receptors, biological material on the sensing film may be detected by the BioFET because the electrical characteristics of the channel region are altered by the presence of the biological material.

Figure 8A:
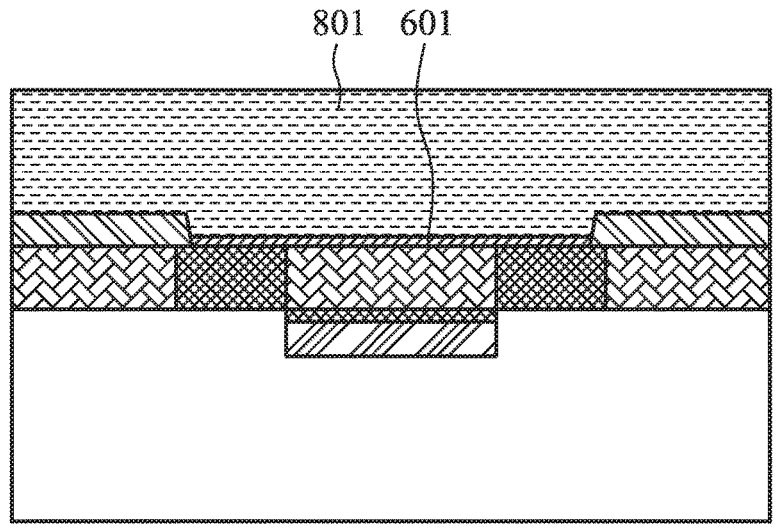
Figure 8B:
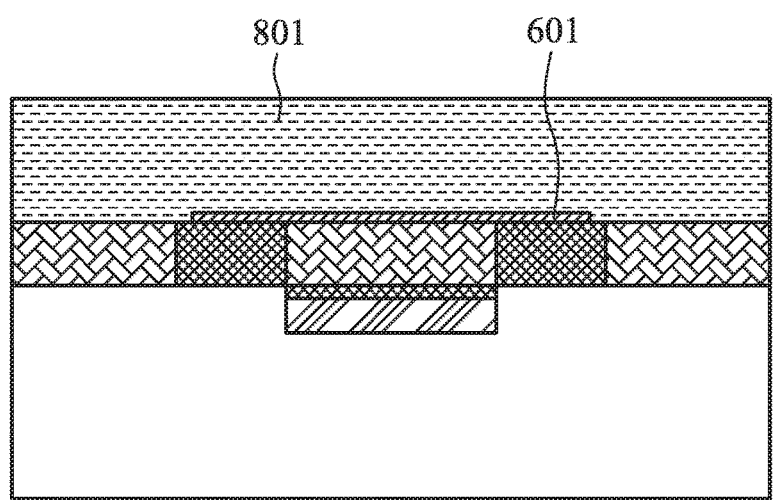
Figure 9A:
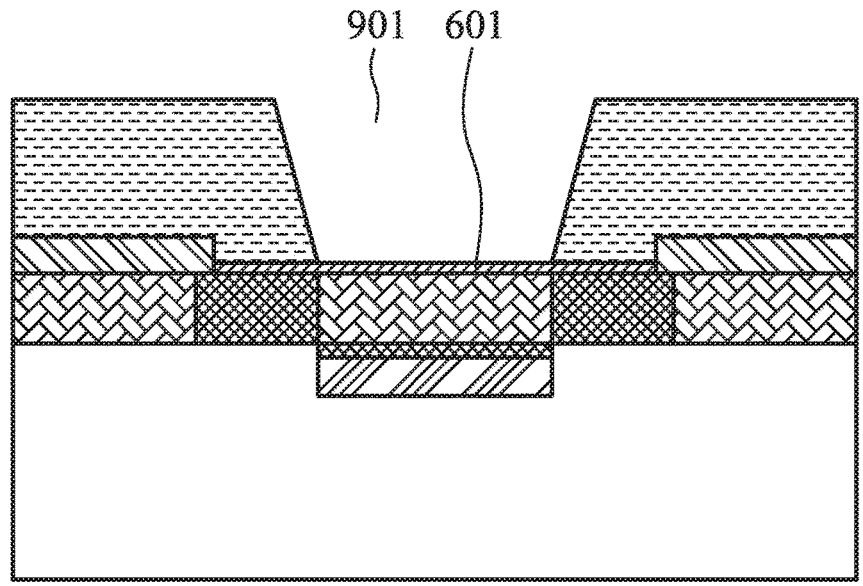
Figure 9B:
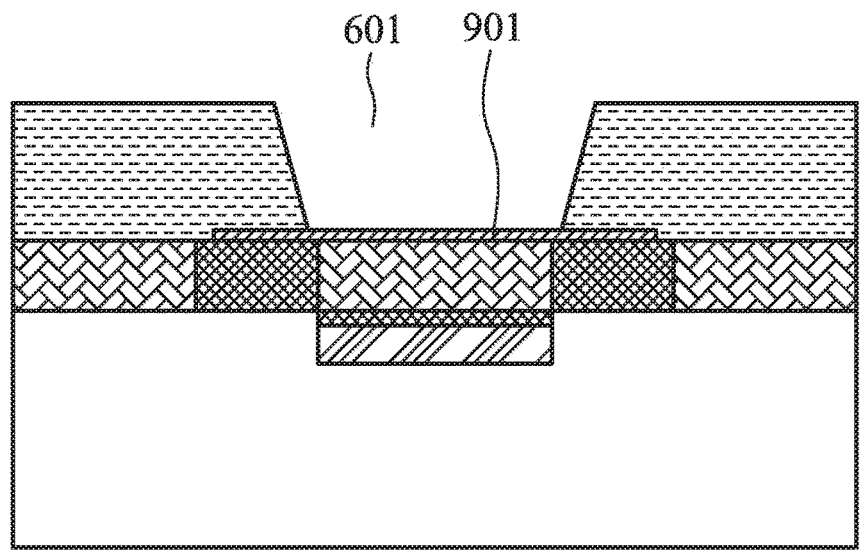

Referring back to FIG. 1A, in block 112 a microfluidic channel or microfluidic well is formed over the sensing film. Block 112 may be performed before or after block 110 of method 100 of FIG. 1A depending on the material used and type of treatment or receptor. For example, some receptors may be damaged during a microfluidic channel or well formation structure. In some embodiments, the microfluidic channel or well is deposited and shaped over the sensing well. FIGS. 8A/8B and 9A/9B are cross section diagrams of microfluidic wells formed over the sensing film. FIG. 8A is an example where a trench 505 is formed over sensing film 601, FIG. 8B is an example where the intrinsic dielectric layer was completely removed and no trench 505 was formed. In both cases, a biocompatible material is deposited over the wafer to form a substantially flat surface. In various examples, the biocompatible material is a biocompatible photoresist. A photoresist may be used because it is shaped easily by using photolithography without affecting the sensing film surface. One example is epoxy-based negative photoresist SU-8™. A photoresist may be transparent and a feature of such microfluidic structure is that it can be observed externally during operation. The photoresist may be deposited using a spin-on tool, patterned by exposure, and developed to remove the wells as shown in FIGS. 9A and 9B. FIGS. 9A and 9B include microfluidic wells 901 formed in the biocompatible material 801. As shown, the microfluidic wells 901 exposes the sensing film 601 (and any coating or receptors thereon) to the biological fluid matter during operation.

In some embodiments, the biocompatible material is not a photoresist. The biocompatible material may be an epoxy, a silicone, for example, polydimethylsiloxane (PDMS), or other organic polymer such as Polyethylene glycol (PEG). The biocompatible material may be deposited in bulk and shaped on the BioFET, for example, by etching. The biocompatible material may also be deposited on the BioFET in a certain shape by molding, for example, by compression molding followed by curing or by injection molding through a mold. The biocompatible material 801 is selected to have good adhesion with portions of the sensing film 601 and the surface of the semiconductor layer between adjacent BioFETs.

Figure 8C:
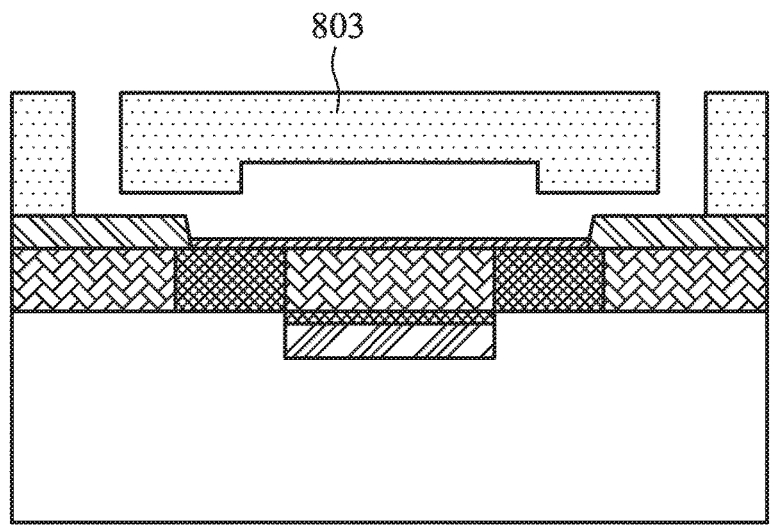
Figure 8D:
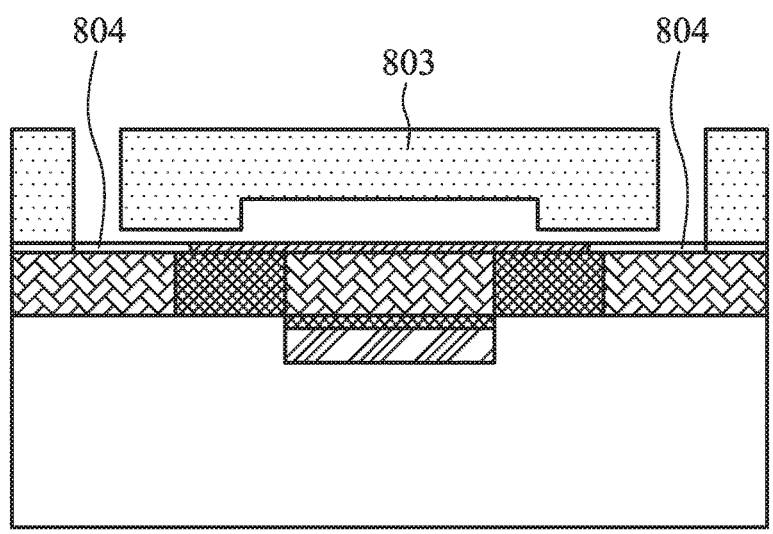

In still other embodiments, a microfluidic channel or well is formed separately from the BioFET and attached in a separate operation. FIGS. 8C and 8D are cross section diagrams that include a pre-formed microfluidic structure 803 that is then attached to the wafer over the sensing film and passivating/blocking layer 804. The microfluidic structure 803 may be formed separately and individually attached to the wafer before the BioFET device is diced. The microfluidic structures 803 may also be formed as a package substrate that maps to the BioFET device on the wafer one to one to allow a wafer level formation of the BioFET device. The microfluidic structures 803 may be attached by anodic bonding or adhesive bonding. The microfluidic structures 803 may include inlets/outlets, wells, channels, and reservoirs operable to hold a fluid. The microfluidic structures 803 may further include material that helps to direct the flow biological matter and conduct analysis. For example, the microfluidic structures 803 may include micropumps and valves and magnetic material or ferromagnetic material for magnetophoresis, metals for electrophoresis, or particular dielectric material for dielectrophoresis.

The microfluidic structure 803 may be fabricated and/or connected or bonded to the BioFET device outside of a CMOS process, for example, the microfluidic structure may be fabricated and/or connected to the device using processes that are not typical of standard CMOS fabrication. In some embodiments a second entity, separate from the entity fabricating the transistors, may connect the microfluidic structure to the BioFET device. A separate formation of the microfluidic structure allows a greater variety of material to be used and larger process window when it is not formed on easily-damaged BioFET. Uniformity of the BioFET surface for attaching the microfluidic structure may become more important as the photoresist-based microfluidic structure would be able to better accommodate surface variations.

Figure 9C:
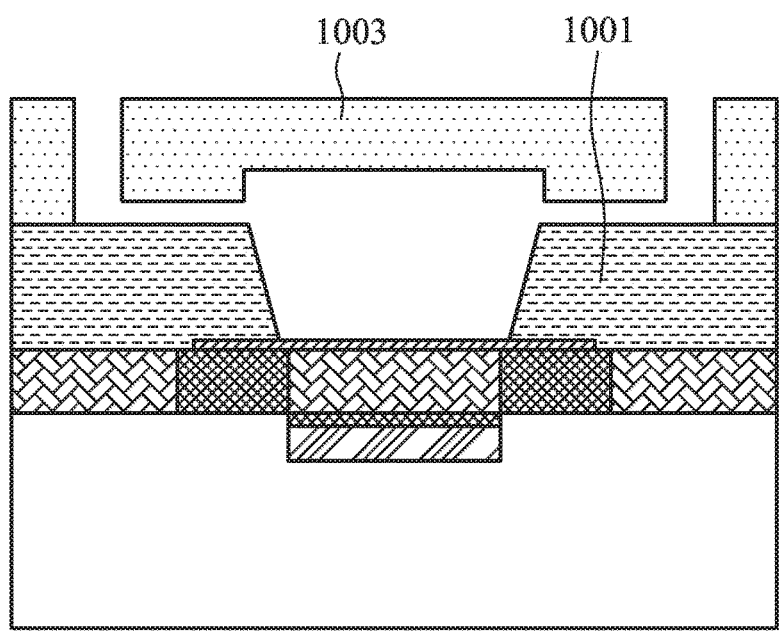

In still other embodiments, the microfluidic structure may be formed using a combination of operations. FIG. 9C is a cross section diagram of a BioFET having a two part microfluidic structure: a microfluidic well structure 1001 formed over the sensing film by deposition and patterning, and microfluidic channels structures 1003 attached to the microfluidic well structure 1001.

One aspect of the present disclosure pertains to a method of manufacturing a biological field-effect transistor (BioFET) that includes forming a FET device on a semiconductor substrate, wherein the FET device includes a gate structure formed on a first surface of the semiconductor substrate and a channel region; exposing the channel region from a second surface of the semiconductor substrate, wherein a surface of the channel region is exposed by a non-plasma etch; and forming a sensing film on the channel region of the second surface of the semiconductor substrate in the opening. The method may also include thinning the semiconductor substrate from a second surface; or forming a receptor on the sensing film, wherein the receptor is selected from the group consisting of enzymes, antibodies, ligands, peptides, nucleotides, self-assembled molecules. The sensing film may be $Si_3N_4$, $Al_2O_3$, $TiO_2$, $HfO_2$, $Ta_2O_5$, $SnO$, $SnO_2$, $Ba_xSr_{1-x}TiO_3$ or combinations of these.

Another aspect of the present disclosure pertains to a method of manufacturing a BioFET on an SOI substrate. The method includes forming a FET device on a SOI semiconductor substrate, wherein the FET device includes a gate structure formed on a first surface of the semiconductor substrate and a channel region in the semiconductor substrate below the gate structure; attaching the first surface of the semiconductor substrate to a carrier substrate; exposing the channel region from a second surface of the semiconductor substrate by removing a portion of the semiconductor substrate; forming an sensing film on the channel region of the second surface of the semiconductor substrate in the opening; and, forming a microfluidic channel or microfluidic well over the sensing film.

In yet another aspect, the present disclosure pertains to a device having a carrier substrate, a first BioFET device attached to the carrier substrate, and a microfluidic channel or microfluidic well structure disposed over a sensing film on the first BioFET device. The first BioFET device includes a gate structure on a first side of a semiconductor substrate; a source region and a drain region in the semiconductor substrate adjacent to the gate structure; a channel region interposing the source and drain regions and underlying the gate structure; and, a sensing film directly on and covering at least a portion of the channel region on a second side of the semiconductor substrate.

In describing one or more of these embodiments, the present disclosure may offer several advantages over prior art devices. In the discussion of the advantages or benefits that follows it should be noted that these benefits and/or results may be present is some embodiments, but are not required in every embodiment. Further, it is understood that different embodiments disclosed herein offer different features and advantages, and that various changes, substitutions and alterations may be made without departing from the spirit and scope of the present disclosure.

What is claimed is:
1. A method of using a biological field-effect transistor (BioFET) device, comprising:
providing the bioFET device, the bioFET device having a gate structure formed on a first surface of a semiconductor layer, a channel region in the semiconductor layer below the gate structure, source and drain regions in the semiconductor layer on opposite sides of the channel region,
wherein the gate structure is aligned between the source and drain regions, and a sensing film is directly on the source, drain, and channel regions on a second surface of the semiconductor layer, the second surface being opposite from the first surface; and
disposing a film treatment or a receptor on the sensing film.
2. The method of claim 1, wherein the disposing comprises binding ssDNA strands to the sensing film.
3. The method of claim 1, wherein the disposing comprises binding monoclonal antibodies to the sensing film.
4. The method of claim 1, wherein the disposing comprises binding a self-assembled monolayer (SAM) to the sensing film.
5. The method of claim 4, wherein the SAM includes head groups chosen from the group consisting of silane groups, amine groups, thiol groups, alkyl groups, alkene groups, alkyne groups, azido groups, and expoxy groups.
6. The method of claim 1, wherein the disposing comprises disposing a film treatment on the sensing film configured to change a hydrophobicity of a surface of the sensing film.
7. The method of claim 1, wherein the disposing comprises patterning the receptor on the sensing film using at least one of micro-contact printing, dip-pen nanolithography, or selective removal of the receptor.
8. A method of using a biological field-effect transistor (BioFET) device, comprising:
providing the bioFET device, the bioFET device having a gate structure formed on a first surface of a channel region in a semiconductor layer, source and drain regions in the semiconductor layer on opposite sides of the channel region,
wherein the gate structure is aligned between the source and drain regions, and a sensing film is formed directly on the source and drain regions and on a second surface of the channel region, the second surface being opposite from the first surface; and
disposing a film treatment or a receptor on the sensing film.
9. The method of claim 8, wherein the disposing comprises binding ssDNA strands to the sensing film.
10. The method of claim 8, wherein the disposing comprises binding monoclonal antibodies to the sensing film.
11. The method of claim 8, wherein the disposing comprises binding a self-assembled monolayer (SAM) to the sensing film.
12. The method of claim 11, wherein the SAM includes head groups chosen from the group consisting of silane groups, amine groups, thiol groups, alkyl groups, alkene groups, alkyne groups, azido groups, and expoxy groups.

13. The method of claim 8, wherein the disposing comprises disposing a film treatment on the sensing film configured to change a hydrophobicity of a surface of the sensing film.

14. The method of claim 8, wherein the disposing comprises patterning the receptor on the sensing film using at least one of micro-contact printing, dip-pen nanolithography, or selective removal of the receptor.

15. A method of using a biological field-effect transistor (BioFET) device, comprising:
providing the bioFET device, the bioFET device having a gate structure formed over a channel region in a semiconductor layer, source and drain regions in the semiconductor layer on opposite sides of the channel region, wherein the gate structure is aligned between the source and drain regions, and a sensing film is formed directly on the source, drain, and channel regions and beneath the gate structure, and disposing a film treatment or a receptor on the sensing film.

16. The method of claim 15, wherein the disposing comprises binding ssDNA strands to the sensing film.

17. The method of claim 15, wherein the disposing comprises binding monoclonal antibodies to the sensing film.

18. The method of claim 15, wherein the disposing comprises binding a self-assembled monolayer (SAM) to the sensing film.

19. The method of claim 18, wherein the SAM includes head groups chosen from the group consisting of silane groups, amine groups, thiol groups, alkyl groups, alkene groups, alkyne groups, azido groups, and expoxy groups.

20. The method of claim 15, wherein the disposing comprises patterning the receptor on the sensing film using at least one of micro-contact printing, dip-pen nanolithography, or selective removal of the receptor.

* * * * *